US009816922B2

(12) United States Patent
Lewis

(10) Patent No.: US 9,816,922 B2
(45) Date of Patent: Nov. 14, 2017

(54) DUAL-MODE CHARACTERIZATION OF PARTICULATES

(75) Inventor: E. Neil Lewis, Olney, MD (US)

(73) Assignee: Malvern Instruments Limited, Malvern (GB)

( * ) Notice: Subject to any disclaimer, the term of this patent is extended or adjusted under 35 U.S.C. 154(b) by 0 days.

(21) Appl. No.: 14/239,039

(22) PCT Filed: Aug. 17, 2012

(86) PCT No.: PCT/GB2012/052019
§ 371 (c)(1),
(2), (4) Date: Feb. 4, 2015

(87) PCT Pub. No.: WO2013/027034
PCT Pub. Date: Feb. 28, 2013

(65) Prior Publication Data
US 2015/0146202 A1    May 28, 2015

Related U.S. Application Data

(60) Provisional application No. 61/525,669, filed on Aug. 19, 2011, provisional application No. 61/560,596, (Continued)

(51) Int. Cl.
*G01N 21/00* (2006.01)
*G01N 21/51* (2006.01)
(Continued)

(52) U.S. Cl.
CPC ............... *G01N 21/51* (2013.01); *G01J 3/44* (2013.01); *G01N 15/0205* (2013.01);
(Continued)

(58) Field of Classification Search
CPC ........ G01N 21/65; G01N 21/51; G01N 15/02; G01N 15/14; G01N 21/658; G01N 2021/656; G01J 3/02; G01J 3/44
(Continued)

(56) References Cited

U.S. PATENT DOCUMENTS 4,586,819 A * 5/1986 Tochigi .................. G01N 21/65
356/301
5,506,678 A * 4/1996 Carlsen .................. G01N 21/03
356/301
(Continued)

FOREIGN PATENT DOCUMENTS

EP    1913866    4/2008
EP    2017600    1/2009
(Continued)

OTHER PUBLICATIONS

PCT International Search Report, PCT/GB2012/052019, EPO—Internal, WPI Data, Inspec.
(Continued)

*Primary Examiner* — Abdullahi Nur
(74) *Attorney, Agent, or Firm* — Kristofer E. Elbing

(57) ABSTRACT

The invention relates to methods and apparatus for detecting properties of suspended particles. Embodiments disclosed include an optical instrument (200) for detecting properties of a sample, comprising: a sample cell (103) for holding a sample of a particulate dispersion; a coherent light source (101) configured to illuminate the sample in the sample cell (103); a light intensity detector (104, 106) positioned to receive and measure an intensity of light from the coherent light source (101) elastically scattered by the sample in the sample cell (103); and a spectral light detector (212) positioned and configured to receive and measure a range of wavelengths of light from the coherent radiation source (101) inelastically scattered by the sample in the sample cell (103).

26 Claims, 10 Drawing Sheets

Related U.S. Application Data filed on Nov. 16, 2011, provisional application No. 61/669,004, filed on Jul. 6, 2011.

(51) Int. Cl.
  *G01J 3/44* (2006.01)
  *G01N 15/02* (2006.01)
  *G01N 21/65* (2006.01)
  *G01N 15/14* (2006.01)
  *G01N 21/80* (2006.01)
  *G01N 21/47* (2006.01)

(52) U.S. Cl.
  CPC ......... *G01N 15/1434* (2013.01); *G01N 21/65* (2013.01); *G01N 21/80* (2013.01); *G01N 2021/4709* (2013.01); *G01N 2201/068* (2013.01); *G01N 2201/06113* (2013.01)

(58) Field of Classification Search
  USPC .................................... 356/72–73, 300–445
  See application file for complete search history.

(56) References Cited

U.S. PATENT DOCUMENTS

| | | | |
|---|---|---|---|
| 5,786,893 A * | 7/1998 | Fink | G01N 21/65 356/301 |
| 6,307,626 B1 * | 10/2001 | Miles | G01J 3/44 356/301 |
| 6,507,422 B1 | 1/2003 | Fukushima | |
| 8,018,582 B2 | 9/2011 | Jeong et al. | |
| 2006/0103840 A1 | 5/2006 | Honeywell | |
| 2009/0073438 A1 | 3/2009 | Horiba | |
| 2010/0020312 A1 | 1/2010 | Jeong et al. | |
| 2011/0213252 A1 | 9/2011 | Fulghum | |

FOREIGN PATENT DOCUMENTS

| | | |
|---|---|---|
| JP | 6053834 | 2/1994 |
| JP | 2000146839 | 5/2000 |
| JP | 2002535025 | 10/2002 |
| JP | 2000329682 | 1/2003 |
| JP | 2005306827 | 4/2005 |

OTHER PUBLICATIONS

European Patent Examination Report, Application No. 12 775 274.6-1554, Ref. JL63421P.EPP, dated Oct. 30, 2014, Applicant: Malvern Instruments Ltd.

Lixin Peng et al, "Elastic and Inelastic Light Scattering from Single Bacterial Spores in an Optical Trap Allows the Monitoring of Spore Germination Dynamics", Analytical Chemistry, vol. 81, No. 10, May 15, 2009, pp. 4035-4042.

Anonymous, "Raman Microspectrometer", Application Note 42, Jan. 1, 2009, pp. 1-8, from Internet: http://assets.newport.com/webdocuments-EN/images/14075.pdf (retrieved on Nov. 30, 2012), p. 3, figure 1.

Branca C et al, "Swelling processes in aqueous polymer solutions by PCS and Raman scattering", Journal of Molecular Structure, vol. 482-483, May 25, 1999, Elsevier, Amsterdam, NL, pp. 503-507.

PCT International Search Report, PCT/GB2012/052019, EPO-Internal, WPI Data, INSPEC.

Written Opinion of the International Searching Authority, Application No. PCT/GB2012/052019, PCT ISA/220.

European Patent Examination Report, Application No. 12 775 274.6-1554, Ref. JL63421REPP, Oct. 30, 2014, Applicant: Malvern Instruments Ltd.

Japanese Office Action. Patent Application No. 2014-526551. Apr. 5, 2016.

* cited by examiner

DUAL-MODE CHARACTERIZATION OF PARTICULATES

This application is a National Phase counterpart of PCT/GB2012/052019 claims priority to provisional application No. 61/525,669 filed Aug. 19, 2011 and to provisional application No. 61/560,596 filed Nov. 16, 2011 and to provisional application No. 61/669,004 filed Jul. 6, 2012. All of these applications are herein incorporated by reference.

FIELD OF THE INVENTION

The invention relates to methods and apparatus for detecting properties of suspended particles.

BACKGROUND OF THE INVENTION

There are a number of different ways to characterize complex nanoparticulate materials, such as proteins and large aggregates of proteins. Optical microscopy is a relatively inexpensive technique that can provide a limited amount of size and shape information about cells and highly aggregated proteins. Instruments such as those that perform Dynamic Light Scattering (DLS), Static Light Scattering (SLS), or Size Exclusion Chromatography (SEC) can provide higher resolution information about the size of a wide variety of nanomaterials and nanoparticulates but lack the ability to deliver structural or shape information. More sophisticated instruments such as those that perform Circular Dichroism (CD), Raman spectroscopy, or Fourier Transform Infrared (FTIR) spectroscopy can provide yet molecular structural and conformational information about materials such as proteins but lack the ability to provide any direct information about the size or size distribution of those materials. The most expensive instruments such as those that perform X-ray crystallography and multidimensional Nuclear Magnetic Resonance (NMR) can provide a substantial amount of structural information about complex nanoparticulates, such as larger proteins, but these instruments can cost a million dollars or more and tend not to be particularly useful for routine measurements or for quality assurance or quality control use.

It is an object of the invention to address one or more of the above mentioned problems.

SUMMARY OF THE INVENTION

According to a first aspect of the invention there is provided an optical instrument for detecting properties of a sample, comprising:
  a sample cell for holding a sample of a particulate dispersion;
  a coherent light source configured to illuminate the sample in the sample cell;
  a light intensity detector positioned to receive and measure an intensity of light from the coherent light source elastically scattered by the sample in the sample cell; and
  a spectral light detector positioned and configured to receive and measure a range of wavelengths of light from the coherent radiation source inelastically scattered by the sample in the sample cell.

The spectral light detector may be a Raman detector. The coherent light source may be a laser. The light intensity detector may be a photon-counting detector.

An attenuator may be positioned between one or more of:
  the coherent light source and the sample cell;
  the sample cell and the spectral light detector; and
  the sample cell and the light intensity detector.

The attenuator may be configured to be switchable to provide in a first state a predetermined amount of attenuation for light received by the light intensity detector and in a second state a lesser amount of attenuation for light received by the spectral light detector. The light intensity detector may be configured not to detect light when the attenuator is in the second state.

The optical instrument may comprise a filter configured to transmit a selected range of wavelengths of light from the coherent radiation source inelastically scattered by the sample in the sample cell to the spectral light detector. The filter may be a notch filter.

The spectrometric detector may be configured to receive scattered light from the sample cell along a path orthogonal to incident light from the light source and/or along a path reverse to the incident light for detection of backscattered light.

In certain embodiments, the coherent radiation source may comprise first and second coherent light sources and the light intensity detector may be responsive to light transmitted by the first coherent light source and the spectral light detector responsive to light transmitted by the second coherent radiation source.

Both the light intensity detector and the spectral light detector may be configured to receive and measure light during a measurement period while a property of the sample in the sample cell changes. The property may for example be one or more of pH and temperature.

According to a second aspect of the invention there is provided a method of detecting optical properties of a sample of a particulate dispersion, the method comprising:
  positioning the sample in a sample cell for analysis;
  exciting the sample with incident light from a coherent light source;
  detecting elastically scattered light from the excited sample with a light intensity detector; and
  detecting inelastically scattered light from the excited sample with a spectral light detector.

The sample may be excited with light from a common coherent radiation source during detection of both elastically and inelastically scattered light from the excited sample.

The step of exciting may involve exciting the sample with different coherent radiation sources during the step of detecting elastically scattered radiation and the step of detecting inelastically scattered radiation from the sample.

The step of exciting the sample may be repeated while a condition of the sample is changed. The method may further include the step of performing a correlation between results of the step of detecting elastically scattered radiation from the excited sample and results of the step of detecting inelastically scattered radiation from the excited sample while the condition is changed. The condition may for example be temperature or pH.

The method may further include the step of associating a change in a chemical property of a species in the sample with a changes in the condition based on results of the steps of detecting elastically scattered radiation from the excited sample and detecting inelastically scattered radiation from the excited sample.

The steps of exciting and detecting may be repeated to evaluate one of manufacturability, stability, shelf life, quality control, quality assurance or formulation of the sample.

The steps of positioning, exciting, detecting and removing may be performed for a protein suspension, a biopharmaceutical or for one or more of an enzyme, a protein, a DNA sequence, an RNA sequence, a vaccine, a virus and a virus-like particle.

The method may further including the step of deriving a physical property of the sample from the detected elastically scattered radiation and the step of deriving a chemical property of the sample from the detected inelastically scattered radiation.

The step of deriving a physical property may include deriving a particle size or polydispersity value and the step of deriving a chemical property includes deriving a measure of chemical identification or molecular structure.

The steps of positioning, exciting, detecting and removing may be performed for a protein, and the step of deriving a physical property may include deriving a protein aggregation size distribution and the step of deriving a chemical property may include deriving a protein secondary and tertiary structural information from a Raman measurement.

The step of deriving a chemical property may include deriving information about protein folding or protein denaturation/renaturation.

Systems according to the invention can provide a significant amount of structural and chemical information about nanoparticles and other nanomaterials such as larger proteins at a lesser expense that some of the more expensive X-ray crystallography and multidimensional Nuclear Magnetic Resonance (NMR) instruments. This can come at the price of a relatively simple add-on to an existing DLS/SLS system. In some embodiments, the dual-mode instrument can use a single radiation source to obtain complementary information about both elastic and inelastic scattering.

According to a further general aspect of the invention there is provided an optical instrument for detecting properties of a sample, comprising:
  means for holding a sample for analysis,
  means for exciting the sample,
  means for detecting elastically scattered radiation from the excited sample, and
  means for detecting inelastically scattered radiation from the excited sample.

According to a further general aspect of the invention there is provided an optical instrument for detecting properties of a sample, comprising:
  a vessel for holding the sample;
  one or more coherent radiation sources positioned to illuminate the sample in the vessel;
  a plurality of scattering detectors positioned to receive light from the coherent radiation sources scattered by the sample in the vessel at different angles; and
  at least one spectral detector positioned to receive light from the coherent radiation sources inelastically scattered by the sample in the vessel.

According to a further general aspect of the invention there is provided a method of detecting optical properties of a sample, comprising:
  positioning a sample for analysis;
  performing an inelastic spectral measurement on the sample; and
  deriving information about at least one physical property of the sample from the inelastic spectral measurement based on a prior characterization of the inelastic spectral measurement using another type of measurement.

The step of performing an inelastic spectral measurement on the sample may include performing a Raman measurement.

According to a further general aspect of the invention there is provided an optical instrument for detecting properties of a sample, comprising:
  a vessel for holding the sample,
  one or more coherent radiation sources positioned to illuminate the sample in the vessel,
  at least one photon-counting detector positioned to receive light from the coherent radiation sources elastically scattered by the sample in the vessel, and
  at least one spectral detector positioned to receive light from the coherent radiation sources inelastically scattered by the sample in the vessel.

According to a further general aspect of the invention there is provided a method of detecting optical properties of a sample, comprising:
  positioning a sample for analysis,
  exciting the sample,
  detecting elastically scattered radiation from the excited sample,
  detecting inelastically scattered radiation from the excited sample, and
  removing the sample.

DETAILED DESCRIPTION

The invention is described in further detail below by way of exemplary embodiments and with reference to the accompanying drawings, in which.

Figure 1:
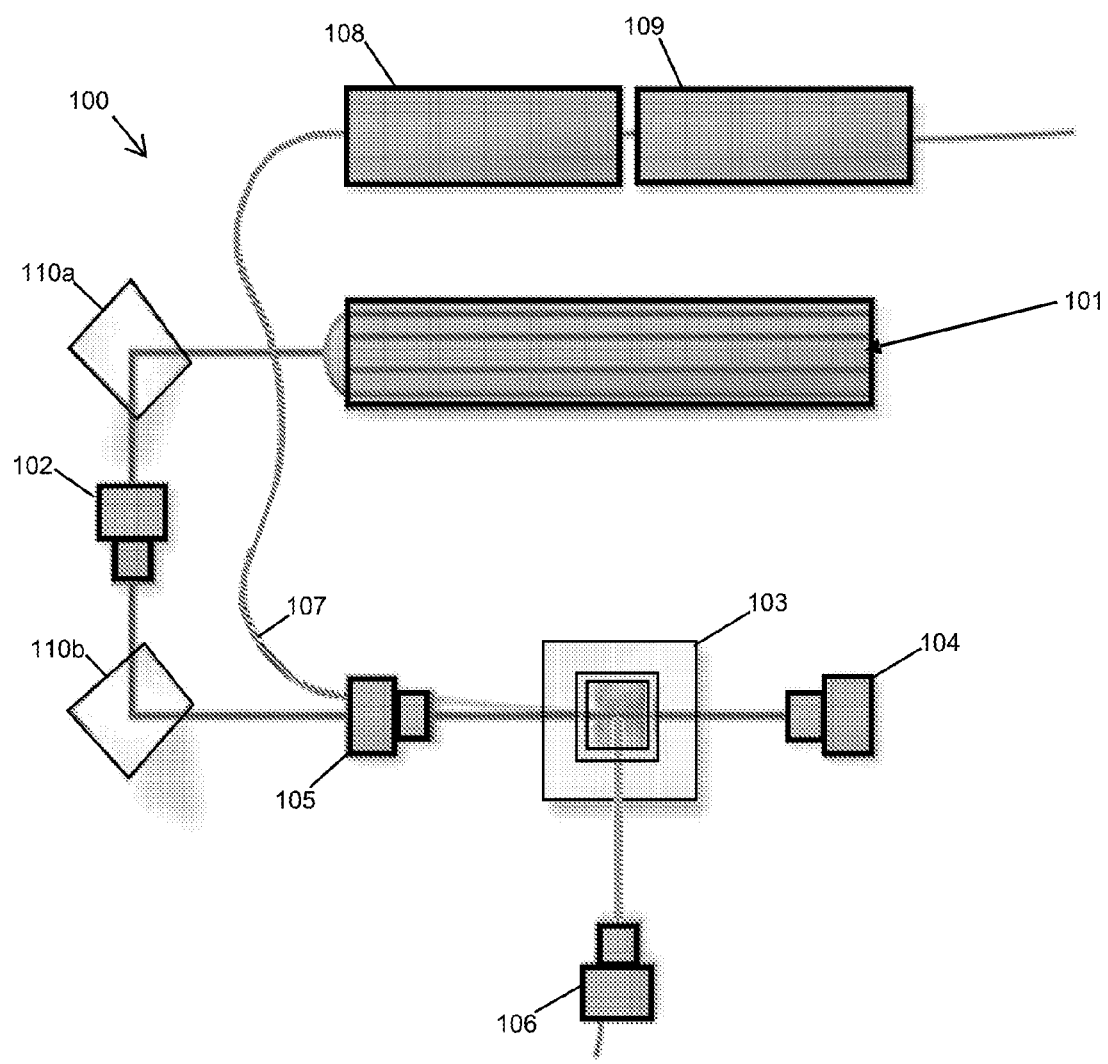
FIG. 1 is a block diagram of a prior art DLS/SLS measurement system that can be used as the basis for an illustrative system according to the invention.

Systems according to the invention can be built from the ground up or may be based on a pre-existing off-the-shelf optical instrument. Such a system can be based on an optical instrument 100 such as the Zetasizer nano particle measurement system, which is outlined schematically in FIG. 1. The Zetasizer particle measurement instrument line is available from Malvern instruments Ltd of Malvern, UK and is described in further detail in WO 2010/04182, the contents of which are incorporated herein by reference.

The particle measurement system 100 includes a coherent radiation source 101, such as a laser. The output of this laser 101 is provided to an attenuator 102, optionally via one or more intervening reflectors 110a, 110b, through a sample cell 103, and on to a transmission monitor 104. Classical 90° optics 106 and/or backscatter optics 105 receive scattered radiation from a suspended particulate sample in the sample cell 103 and measure an intensity of light received from the light source 101 and elastically scattered by the sample in the sample cell 103. The received scattered radiation for one or both of these sets of optics 105, 106 can then be relayed via an optical fiber 107 to an Avalanche Photo Diode (APD) 108. The output of the photodiode 108 can then be correlated using a correlator 109 in the case of DLS, or integrated using an integrator in the case of SLS (not shown).

Figure 2:
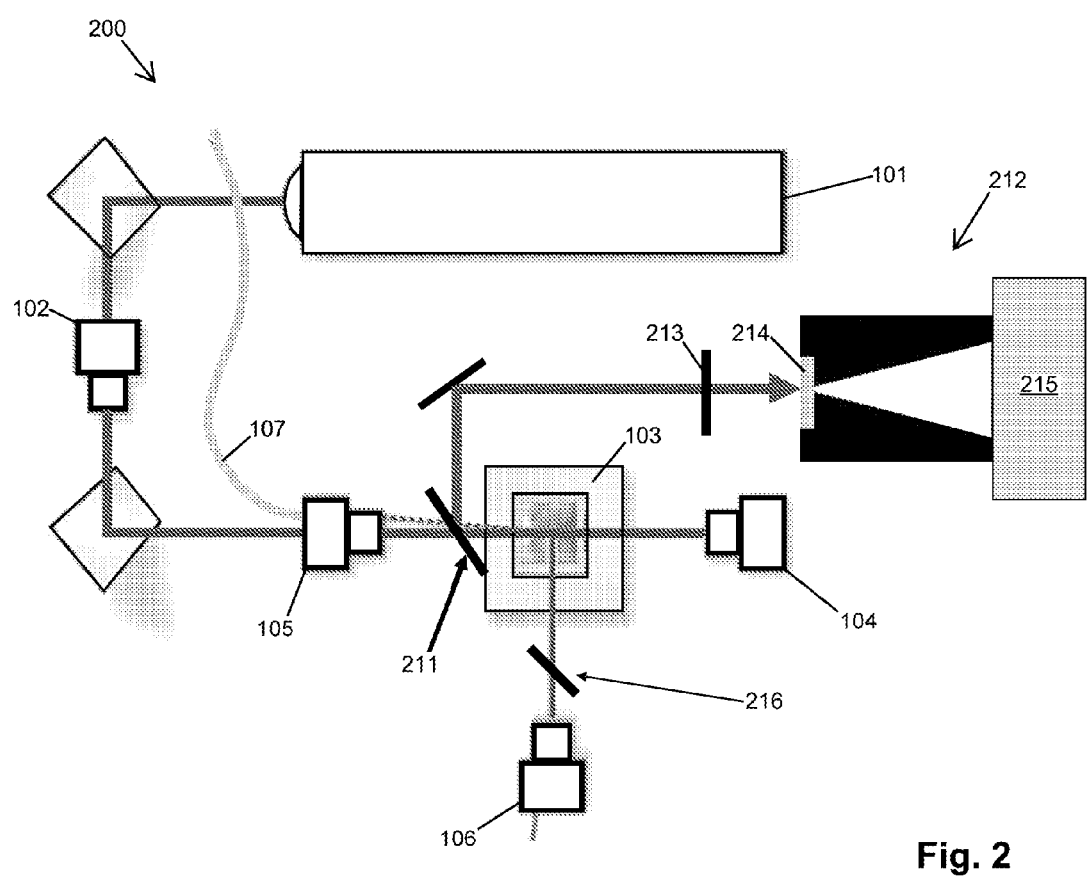
FIG. 2 is a block diagram of an illustrative embodiment of a dual-mode scattering system according to the invention based on the DLS/SLS measurement system of FIG. 1.
Figure 3:
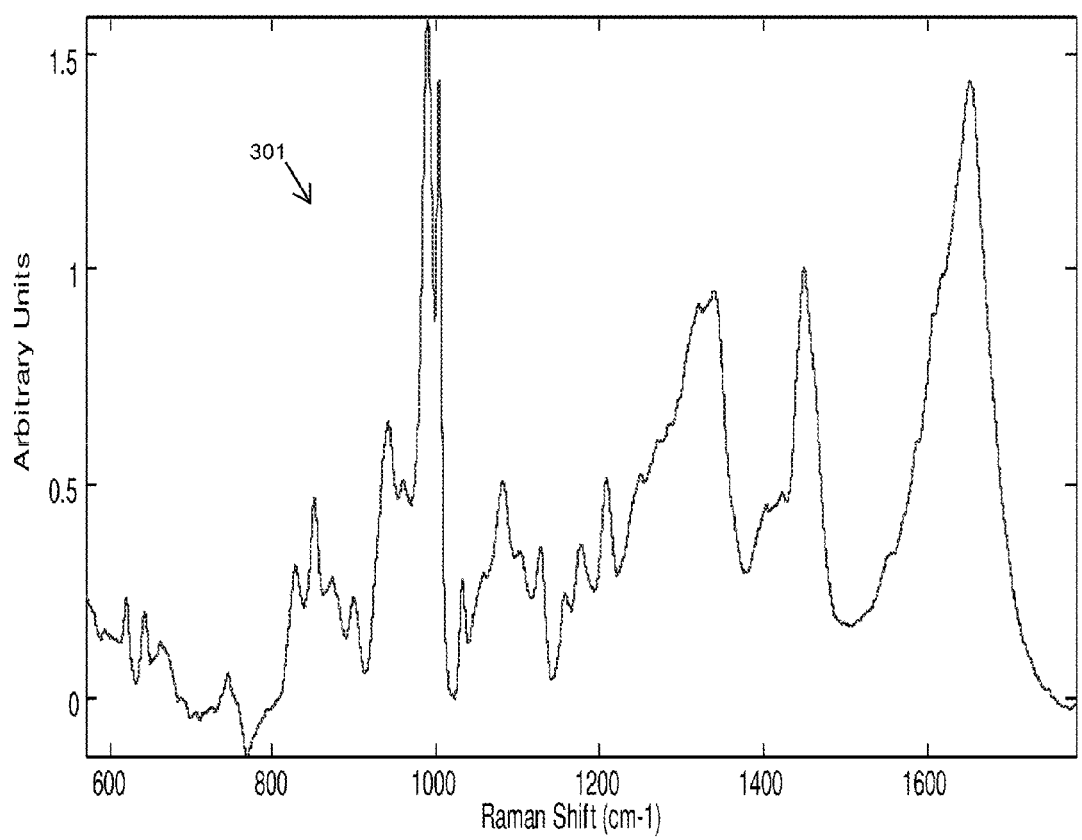
FIG. 3 is an illustrative Raman spectrum for a 50 mg/ml solution of BSA at 61° C. obtained with the system of FIG. 2.

Referring to FIGS. 2 and 3, one approach to modifying the system 100 of FIG. 1 to achieve dual-mode detection in accordance with an aspect of the invention is to add a dielectric filter 211 in the backscatter path. This dielectric filter 211 relays longer wavelength light to a spectrometric detector 212, such as a Raman detector. The Raman detector 212 can include one or more laser notch filters 213, a diffraction grating 214, and a dimensional detector 215, such as a Charge Coupled Device (CCD). Although Raman detection is shown in FIG. 2 to take place in the backscatter path, it can also or alternatively take place from one or more of a number of different angles including from a pickoff point 216 in the classical 90° path. In a general aspect therefore, the spectrometric detector 212 may be configured to receive scattered light from the sample cell along a path orthogonal to the incident light and/or along a path reverse to the incident light for detection of backscattered light.

In operation, the laser 101 in the system 200 of FIG. 2 is used for both DLS and Raman measurements. During DLS measurements, the attenuator 102 is turned on so that the APD 108 (FIG. 1) is not saturated. During Raman measurements, the attenuator 102 is turned off to allow the high level of illumination used in Raman measurements. By alternating between DLS and Raman measurements, the system 200 can acquire information about both elastic and inelastic scattering. These two types of detection can provide complementary information about a particular suspension. For example, DLS measurements can provide information about the aggregation of particulates, while Raman measurements can provide information about the cause of the aggregation or whether the structure of individual particles has changed. This can be helpful in investigating the aggregation of biopharmaceuticals, which can be a serious problem in that they can lose their efficacy and even be harmful when they aggregate. The instrument 200 can also be used to compare one particulate suspension with another. This may be useful for example when comparing one biopharmaceutical formulation from one company with a biosimilar manufactured by another company.

There are a number of other ways to build a system that is configured to obtain these types of complementary information. For example, a system can be built with separate sources for the different measurements organized around separate optical paths. The system can also employ a different arrangement of optical elements and/or different selective or switching elements, such as moving mirrors or choppers, to make both types of measurements. In one embodiment, for example, the attenuator 102 can be placed in the fiber optic 107 path, allowing DLS and Raman measurements to be taken simultaneously.

Figure 4:
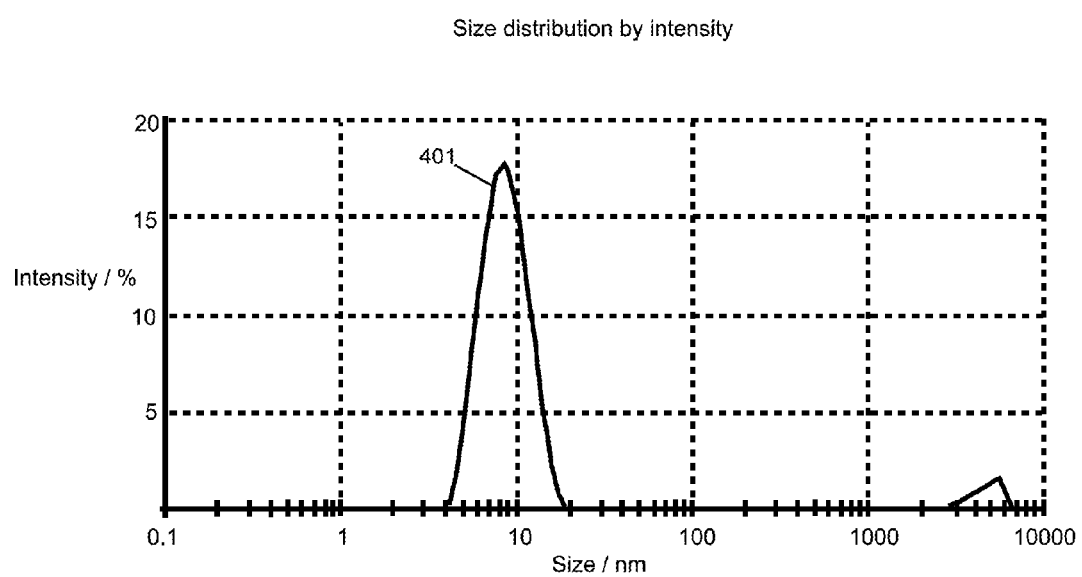
FIG. 4 is an illustrative size distribution plot for the 50 mg/ml solution of BSA at 61° C. obtained with the system of FIG. 2.
Figure 5:
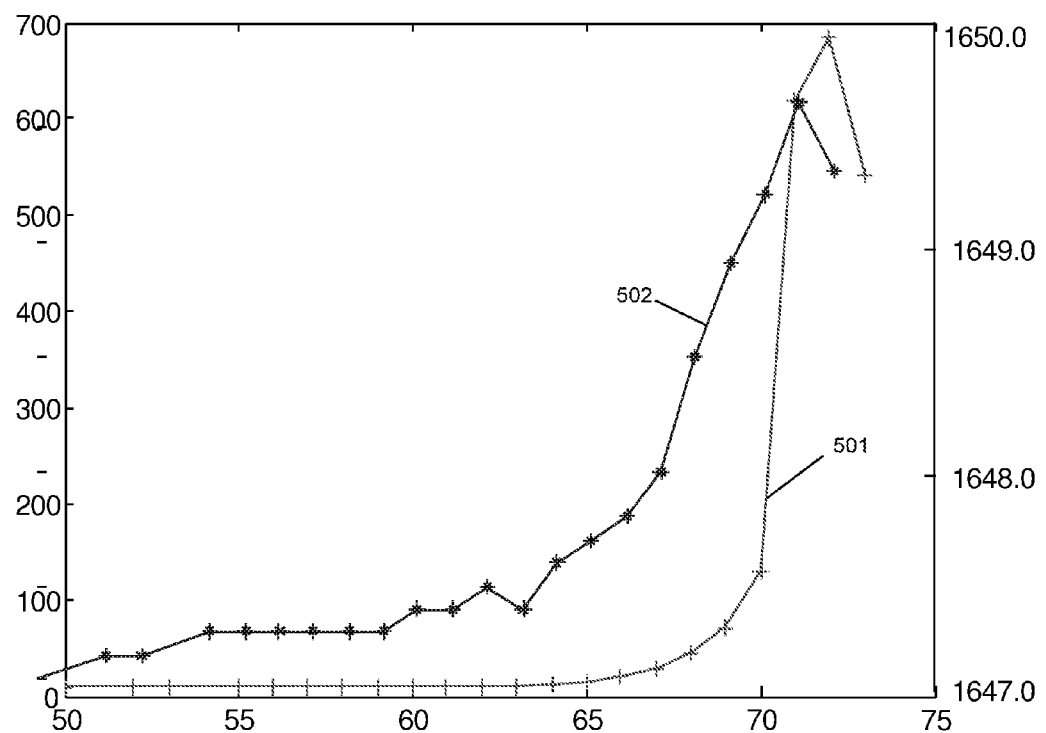
FIG. 5 is an illustrative combined plot of Raman and DLS size measurements for a range of different temperatures obtained with the system of FIG. 2.

Referring to FIGS. 3 to 5, the system 200 of FIG. 2 can be operated to provide spectral information, such as a Raman spectrum 301 (FIG. 3) and physical property information, such as a size distribution 401 (FIG. 4) for the same sample at effectively the same time. These measurements can also be taken in succession under different conditions, such as sample temperature, concentration, pH or composition. FIG. 5 illustrates plots of DLS average size data 501 (left hand scale, in nm) and Raman shift data 502 (right hand scale, in $cm^{-1}$) as a function of temperature (in ° C.) for a protein solution. As the temperature increases, the DLS size data indicates an increase in particle size, indicating aggregation of the protein, while the Raman shift information indicates a structure change in the protein, which in this case is interpreted as a loss of alpha helix. In a general aspect therefore, both the light intensity detector and the spectral light detector are configured to receive and measure light during a measurement period while a property of the sample in the sample cell changes. The property of the sample may be deliberately changed, such as by changing the pH or temperature of the sample, or may change as a result of an ongoing reaction while the sample is being measured. The advantage of such dual measurements is therefore clear, in that different measurements can be taken on the same sample over the same measurement period by alternating between DLS and Raman measurements. The measurements can be performed manually, or may alternatively be performed automatically using standard robotic loading systems, such as x-y stages or using automated pipetting systems.

To derive information from the measurements, such as size distributions or chemical information, the optical instrument system according to embodiments of the invention may be implemented in connection with special-purpose software programs running on general-purpose computer platforms, in which stored program instructions are executed on a processor. The system could also be implemented in whole or in part using special-purpose hardware to achieve the same function. While the system can be broken into the series of modules and steps shown for illustration purposes, one of ordinary skill in the art would recognize that it is also possible to combine them and/or split them differently to achieve a different breakdown.

Figure 6:
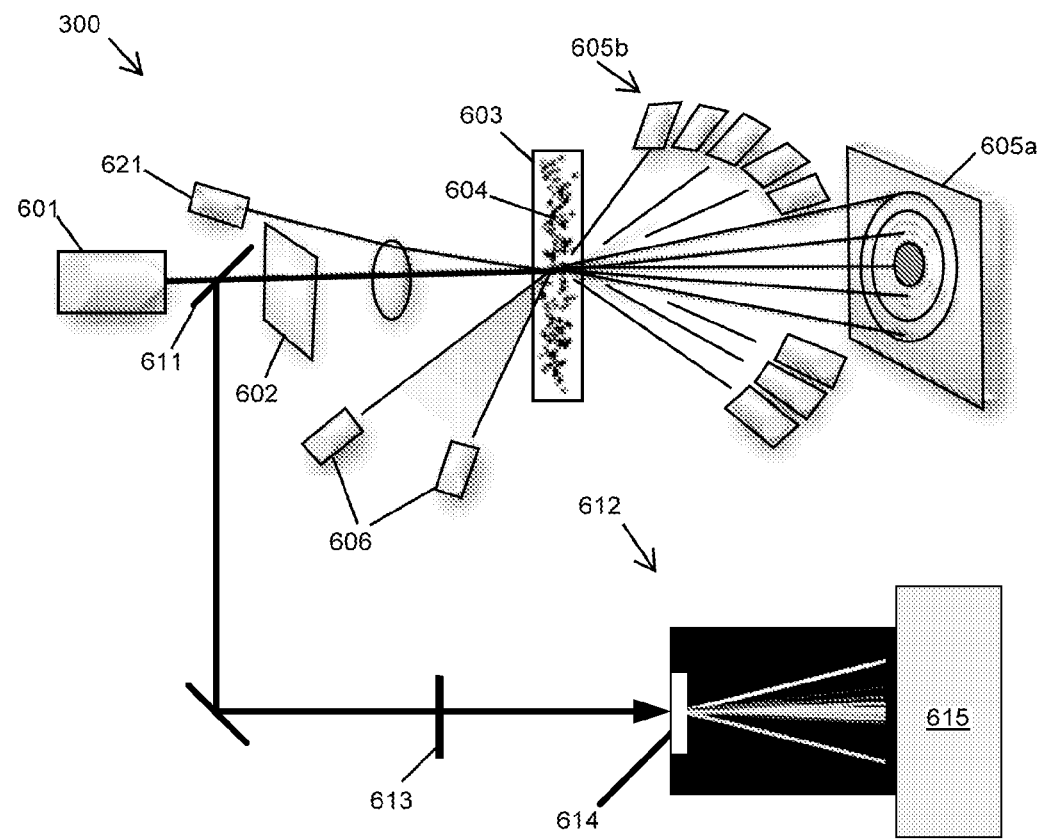
FIG. 6 is a block diagram of an illustrative embodiment of a dual-mode scattering system according to an alternative embodiment based on a laser diffraction measurement system.

Referring to FIG. 6, another approach to dual-mode characterization of particulates is to perform simultaneous Raman and laser diffraction measurements. The technique of laser diffraction is based around the principle that particles passing through a laser beam will scatter light at an angle that is directly related to their size. As the particle size decreases, the observed scattering angle increases logarithmically. The observed scattering intensity is also dependent on particle sizes and diminishes, to a good approximation, in relation to the particle's cross-sectional area. Large particles therefore scatter light at narrow angles with high intensity, whereas small particles scatter at wider angles but with low intensity. The primary measurement that is carried out within a laser diffraction system is the capture of the light scattering data from the particles under study.

Systems according to this aspect of the invention can be built from the ground up or they can be based on a pre-existing off-the-shelf instrument. In one embodiment, such a system can be based on the Mastersizer 3000 particle size analyzer, which is available from Malvern instruments Ltd of Malvern, UK. An exemplary system 300, illustrated schematically in FIG. 6, comprises a coherent light source such as a red laser 601 with an optional attenuator 602, for providing a source of coherent, intense light of a fixed wavelength. An optional second coherent light source such as a blue laser 621 may also be provided. The system 300 further comprises a sample presentation system such as a sample cell 603 configured to pass a material under test through the incident laser beam, preferably as a homogeneous stream of particles 604 in a known, reproducible state of dispersion.

A first series of detectors, including a focal plane detector 605a and an array of large angle detectors 605b, are provided to measure the light pattern produced over a wide range of angles by scattering of incident light by the dispersed particles in the sample cell 603. A second series of detectors 606, 612 are provided to measure backscattered light from the sample cell 603 and for Raman detection. A dielectric filter 611 may be placed in one of the backscattered light paths, the filter 611 configured to relay longer wavelength light to a spectrometric detector such as a Raman detector 612. The Raman detector 612 can include one or more laser notch filters 613, a diffraction grating 614, and a dimensional detector 615, such as a Charge Coupled Device (CCD). Although Raman detection is shown to take place in one of the backscatter paths, it can also or alternatively take place from one or more of a number of different angles including from a pickoff point in the classical 90° path, as in the embodiment of FIG. 2 described above.

In operation, the laser 601 (and/or 621) in the system 300 of FIG. 6 is used for both laser diffraction and Raman measurements. During laser diffraction measurements, the attenuator 602 is turned on so that the scattering detectors are not saturated. During Raman measurements, the attenuator 602 is turned off to allow the high level of illumination used in Raman measurements. By alternating the laser diffraction and Raman measurements, the system can acquire complementary information about a particular suspension. For example, the laser diffraction measurements can provide information about physical properties of the sample, while the Raman measurements can provide information about the chemical makeup of the sample.

As with other embodiments, there are a number of other ways to build a system that obtains these types of complementary information. For example, a system can be built with separate sources for the different measurements organized around separate optical paths. The system can also employ a different arrangement of optical elements and/or different selective or switching elements, such as moving mirrors or choppers, to make both types of measurements. In one embodiment, for example, the attenuator 602 can be placed in such a way as to allow laser diffraction and Raman measurements to be taken simultaneously.

The size range accessible during the measurement is directly related to the angular range of the scattering measurement. Modern laser diffraction instruments make measurements from around 0.02 degrees through to 135 degrees. A logarithmic detector sequence, where the detectors 605 are grouped closely together at small angles and more widely spaced at wide angles, yields the optimum sensitivity. The detector sequence can also be set up such that equal volumes of particles of different sizes produce a similar measured signal. With this approach, the size of the detectors is increased as the measured scattering angle increases.

Once simultaneous measurements have been performed a relationship between the measurements can be established. This can provide further insight into the sample and/or allow one measurement to derive information that another other might ordinarily be used to measure. This approach is described in more detail in connection with the following example.

Example 1

Figure 7:
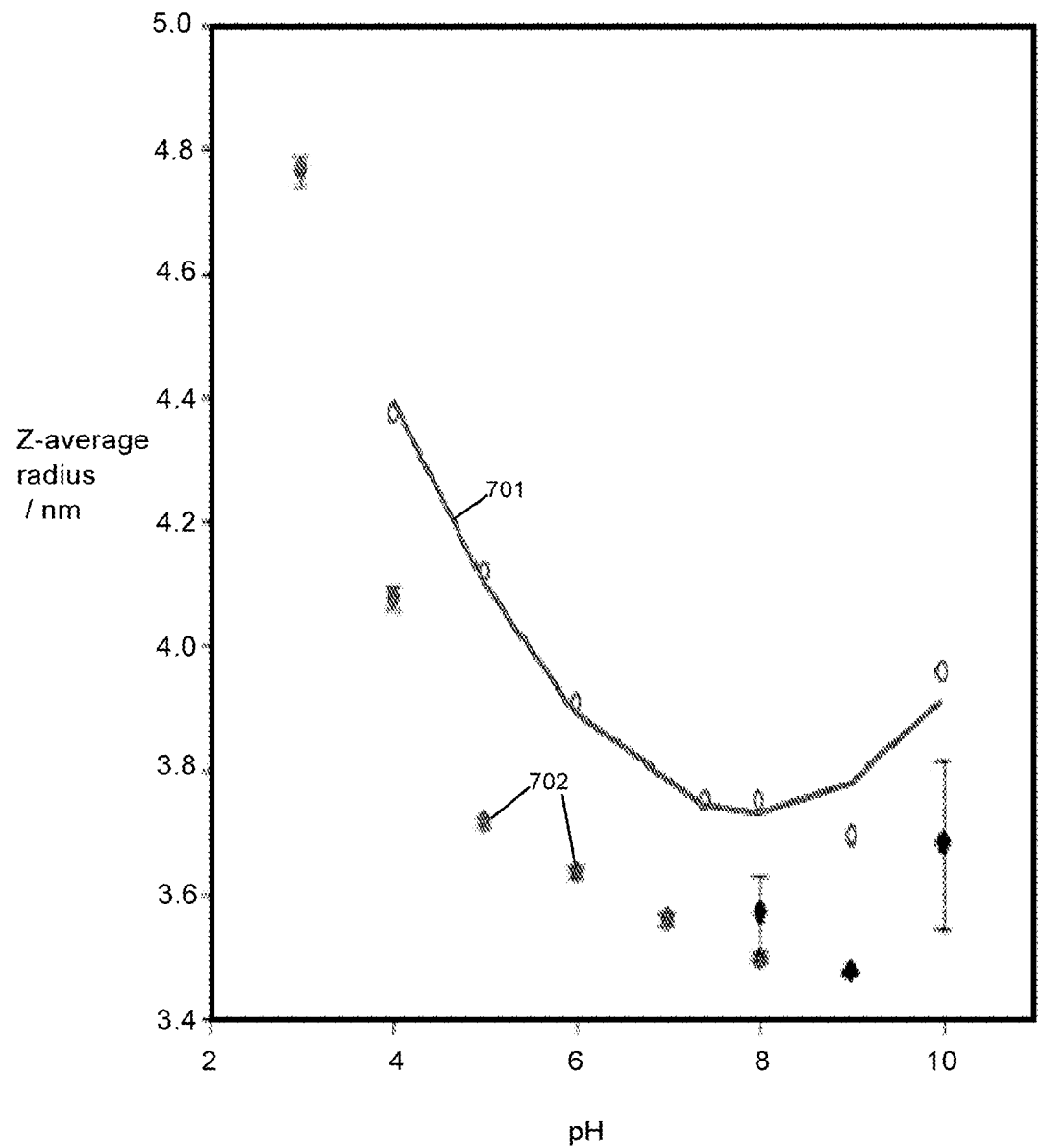
FIG. 7 is a graph showing plots of z-average radius and Raman Amide III intensity (1297 $cm^{-1}$) as a function of pH for a sample of BSA during a titration

Referring to FIG. 7, dual-mode Raman and DLS measurements were performed for a sample of Bovine Serum Albumin (BSA) at different pH levels. As the pH was increased, the DLS measurements 701 showed a trend indicating a change in particle size. At the same time, the Raman measurements 702 also changed in a way that was correlated with changes in the DLS measurements. It is believed that the changes in both the DLS and Raman measurements were caused by the unfolding of the protein resulting from the pH changes. This unfolding is believed to have caused an increase in the size of the molecule, and also a measurable change in the secondary structure of the protein as it unfolds.

Example 2

Figure 8:
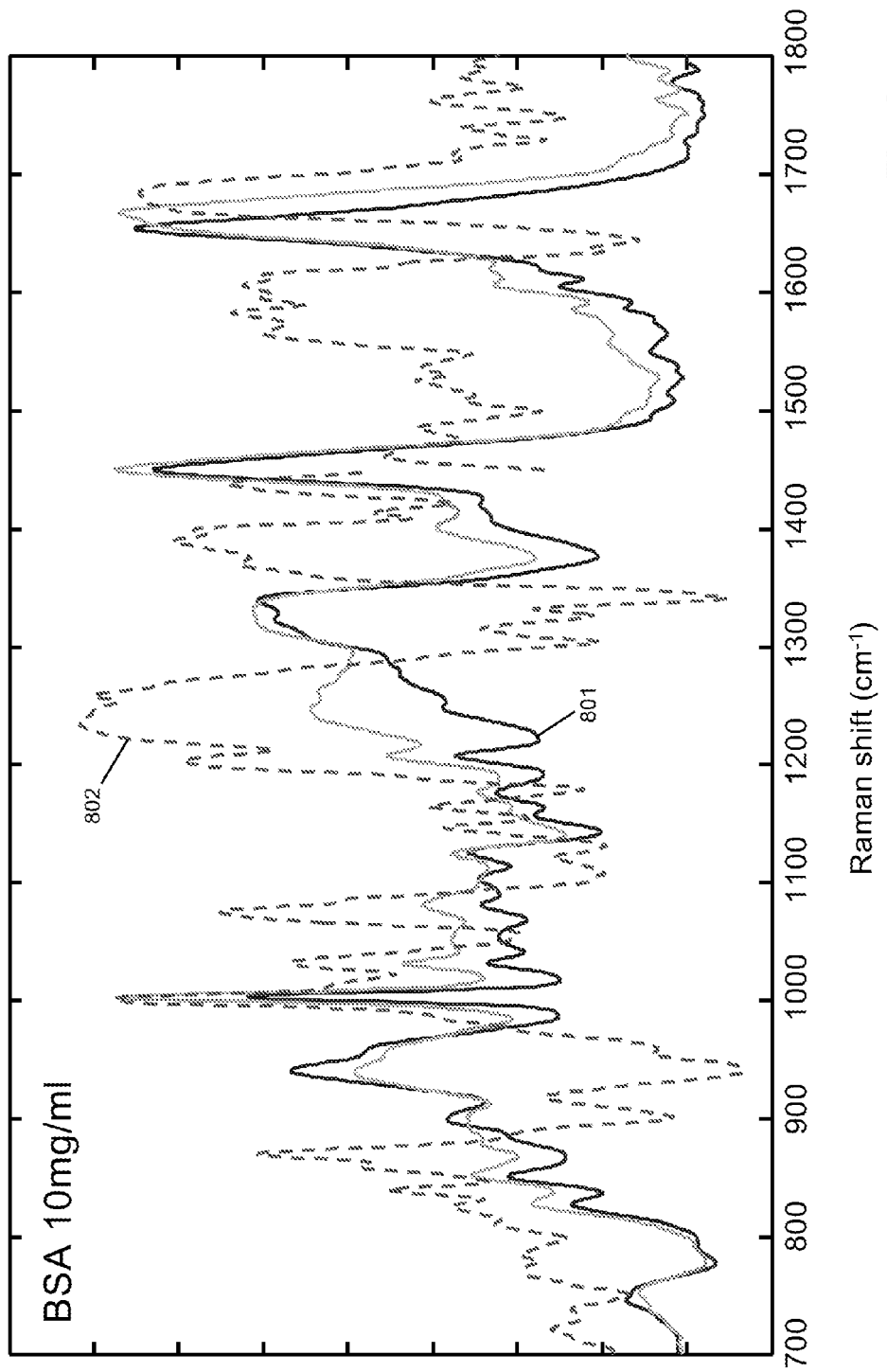
FIG. 8 is a plot of Raman shift measurements and a correlation with DLS size measurements for a BSA 10 mg/ml solution.
Figure 9:
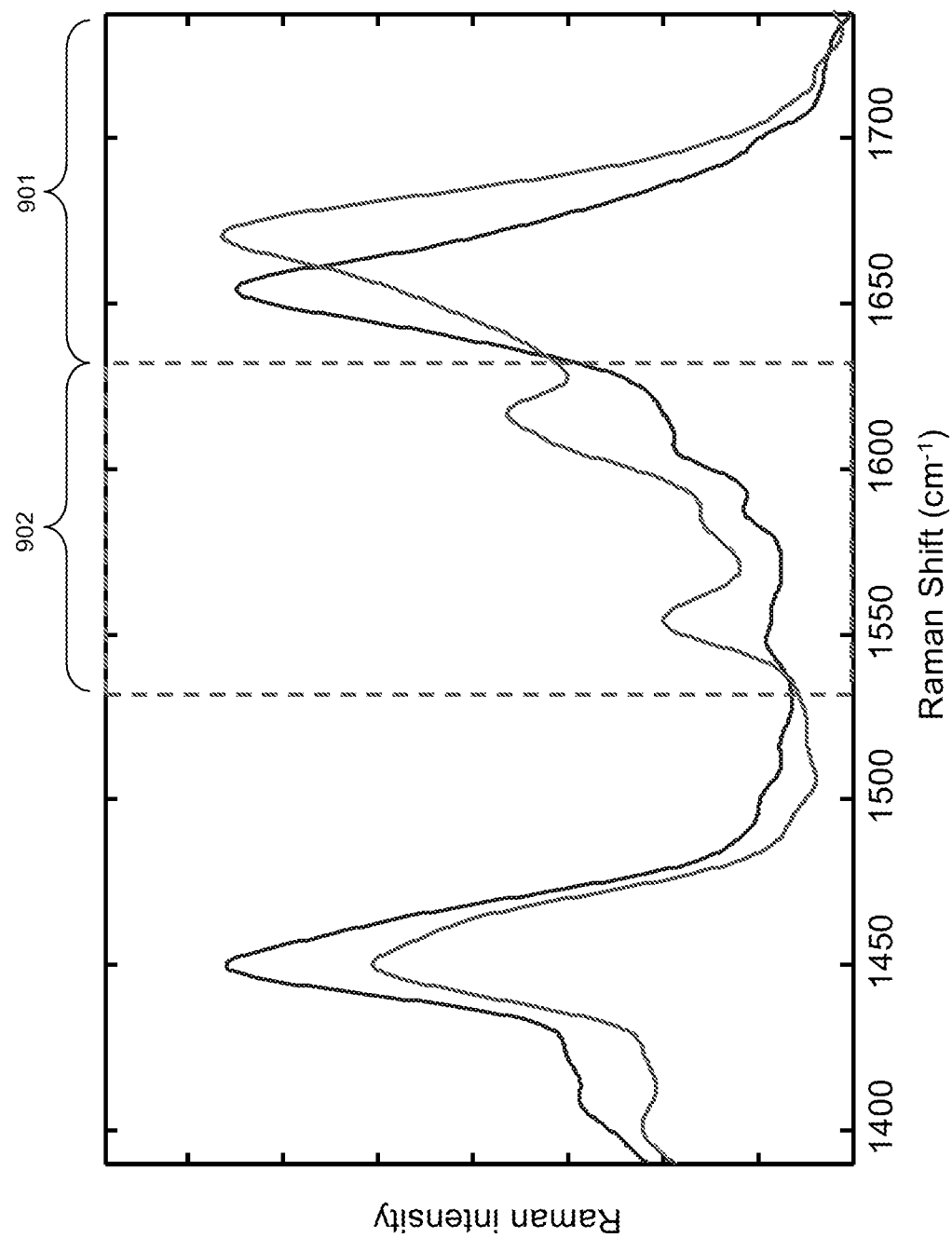
FIG. 9 is a plot of Raman intensity as a function of Raman shift for 10 mg/ml solutions of BSA and IcG.
Figure 10:
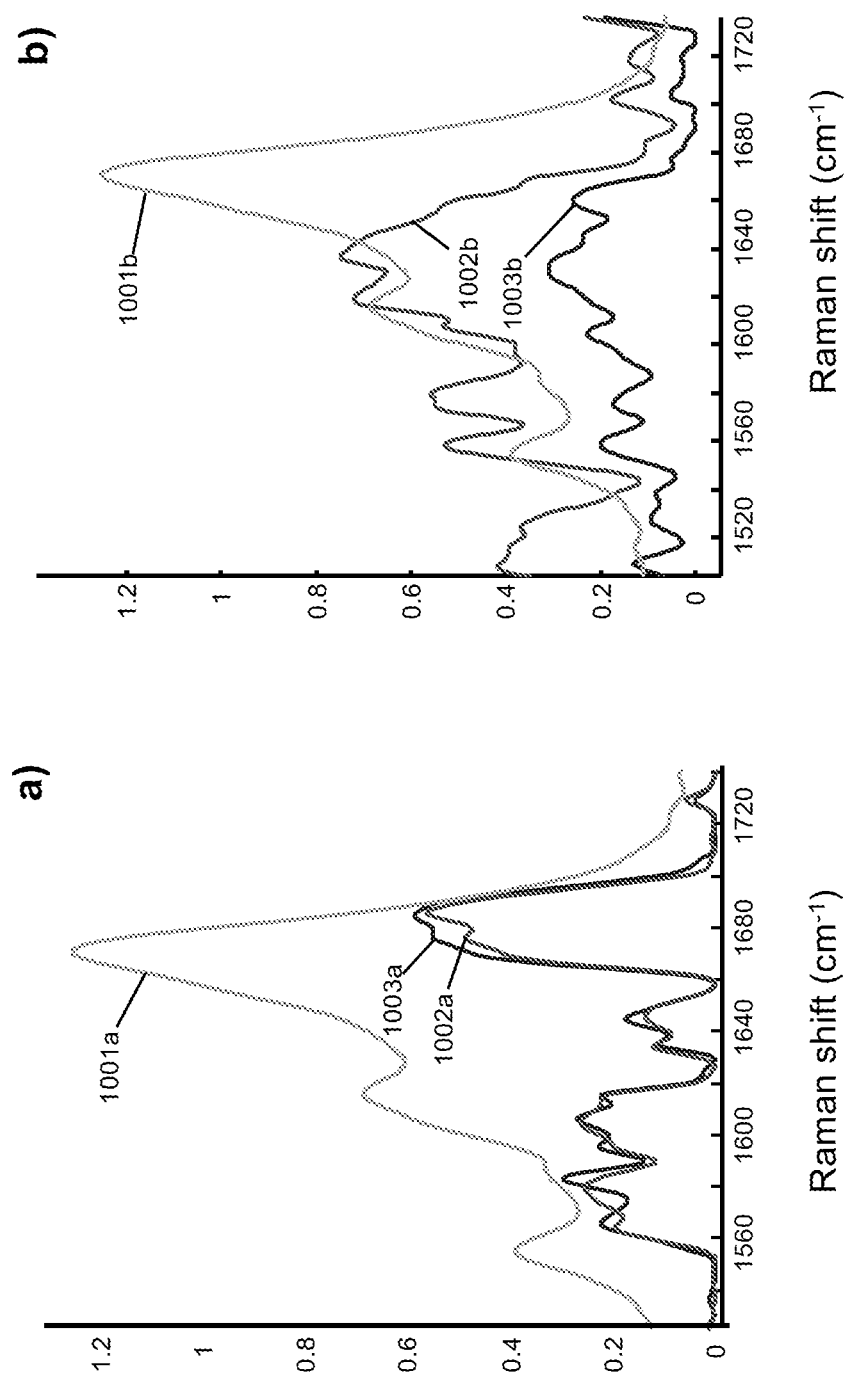
FIG. 10 shows plots of Raman intensity as a function of Raman shift for BSA (FIG. 10a) and IgG (FIG. 10b) solutions, together with correlations with DLS polydispersity and size.

Referring to FIGS. 8 to 10, dual-mode Raman and DLS measurements were performed for a sample of Bovine Serum Albumin (BSA) at different temperature levels. As the temperature was increased, DLS measurements and Raman measurements 801 (FIG. 8) were taken and recorded. These two sets of values were correlated to produce a plot (dotted line 802) that indicates how well size changes correlate with changes in the Raman spectrum at different wavelengths. The experiment was then repeated with Immunoglobulin G (IgG).

Temperature adjustments were used in this first part of the experiment, but other physical properties can be varied, such as pH. While the DLS size parameter was used in this instance, other DLS parameters can also be used, such as polydiversity, which provides a measurement of the distribution of sizes in a sample.

As shown in FIG. 9, chemical structural features correspond to different parts of the Raman spectrum of a compound. A large peak in a first region 901 at higher Raman shifts, for example, corresponds to the backbone of both BSA and IgG, while smaller peaks in a second region 902 at somewhat lower shifts correspond to aromatic side-chains. This knowledge can provide insight into the way that a physical property affects a molecule.

As shown in FIGS. 10a and 10b, correlation plots between DLS and Raman measurements show stronger correlations at different wavelengths. FIG. 10a illustrates a plot of Raman measurements 1001a and correlations with DLS polydispersity 1002a and size 1003a for BSA, while FIG. 10b illustrates Raman measurements 1001b and correlations with DLS polydispersity 1002b and size 1003b for IgG. These correlations can be matched with corresponding molecular features to determine which features are likely to have been affected by the physical changes. Using this technique it can be shown, for example, that a protein denatures and/or aggregates differently in response to changes in temperature than it does in response to changes in pH.

Experiments for other types of changes such as temperature, salt concentration, drug or other chemical concentration, ionic strength, and/or level of denaturation, could also be performed. These types of dual-mode experiments could also be performed to determine other types of chemical and physical properties of different materials. For example, Raman measurements could be used to detect crystallinity of a sample and laser diffraction used to detect size of the sample, while a condition of the sample is varied. This may allow a deeper understanding of the degree to which a sample exhibits crystalline, amorphous, and/or polymorphic properties in different conditions. With this type of understanding, it is possible to perform Raman measurements to learn information about physical properties of a sample in a particular system, such as size, shape, diameter, or aspect ratio. It is also possible to learn about other properties that might otherwise be measured using DLS, including physicochemical properties, such as the protein zeta potential, charge or isoelectric point. This cross-measurement principle can be used between any types of measurements in a dual-mode system according to different schedules. In a quality control situation, for example, a material under test might be fully characterized with both measurement techniques, but routine testing might then be performed with only one of them. The selected technique for routine testing might be selected for a variety of reasons, such as because it is less expensive, quicker, more scalable, or more reliable.

Systems according to the invention can be applicable to a wide variety of applications, including research, quality control, formulation development, stability testing, manufacturability testing, efficiency testing, release testing, and drug discovery. They are also applicable to a wide variety of materials, such as biopharmaceuticals, small- and large-molecule proteins, excipients, and pigments and other industrial powders.

The present invention has been described in connection with a number of specific embodiments thereof. However, numerous modifications which are contemplated as falling within the scope of the present invention should also be apparent to those skilled in the art. Therefore, it is intended that the scope of the present invention be limited only by the appended claims. In addition, the order of presentation of the claims should not necessarily be construed to limit the scope of any particular term in the claims.

The invention claimed is:

1. An optical instrument for detecting properties of a sample, comprising:
    a sample cell for holding a sample of a particulate dispersion;
    a coherent light source configured to illuminate the sample in the sample cell;
    a light intensity detector positioned to receive and measure light intensities from the coherent light source elastically scattered by the sample in the sample cell, wherein the light intensity detector is a dynamic light scattering detector; and
    a spectral light detector positioned and configured to receive and measure a range of wavelengths of light from the coherent radiation source inelastically scattered by the sample in the sample cell, wherein the spectral light detector is a Raman detector, wherein both the light intensity detector and the spectral light detector are configured to successively receive and measure light during a measurement period during which a property of the sample in the sample cell changes, and wherein the property is one or more of pH and temperature.

2. The optical instrument of claim 1 wherein the coherent light source is a laser.

3. The optical instrument of claim 1 further including an attenuator positioned between one or more of:
    the coherent light source and the sample cell;
    the sample cell and the spectral light detector and
    the sample cell and the light intensity detector.

4. The optical instrument of claim 3 wherein the attenuator is configured to be switchable to provide in a first state a predetermined amount of attenuation for light received by the light intensity detector and in a second state a lesser amount of attenuation for light received by the spectral light detector.

5. The optical instrument of claim 4 wherein the light intensity detector is configured not to detect light when the attenuator is in the second state.

6. The optical instrument of claim 1 comprising a filter configured to transmit a selected range of wavelengths of light from the coherent radiation source inelastically scattered by the sample in the sample cell to the spectral light detector.

7. The optical instrument of claim 6 wherein the filter is a notch filter.

8. The optical instrument of claim 1 wherein the spectrometric detector is configured to receive scattered light from the sample cell along a path orthogonal to incident light from the light source and/or along a path reverse to the incident light for detection of backscattered light.

9. The optical instrument of claim 1 wherein the coherent radiation source comprises first and second coherent light sources and wherein the light intensity detector is responsive to light transmitted by the first coherent light source and the spectral light detector is responsive to light transmitted by the second coherent radiation source.

10. The apparatus of claim 1 wherein the instrument is operative to automatically perform the Raman and dynamic light scattering measurements on the sample of a particulate dispersion.

11. The apparatus of claim 1 further including a robotic loading system and wherein the instrument is operative to automatically perform the Raman and dynamic light scattering measurements for a plurality of samples using the robotic loading system.

12. The apparatus of claim 1 wherein both the light intensity detector and the spectral light detector are configured to successively receive and measure light during a measurement period during which a temperature of the sample in the sample cell changes.

13. The apparatus of claim 1 wherein both the light intensity detector and the spectral light detector are configured to successively receive and measure light during a measurement period during which a pH of the sample in the sample cell changes.

14. A method of detecting optical properties of a sample of a particulate dispersion, the method comprising:
    positioning the sample in a sample cell for analysis;
    exciting the sample with incident light from a coherent light source
    detecting elastically scattered light from the excited sample with a light intensity detector;
    detecting inelastically scattered light from the excited sample with a spectral light detector;
    wherein successive steps of exciting the sample, detecting elastically scattered light and detecting inelastically scattered light are repeated under different sample conditions;
    wherein the sample conditions are temperature or pH; and
    wherein the step of detecting elastically scattered radiation comprises performing a Raman measurement, and the step of detecting inelastically scattered radiation comprises performing a DLS measurement.

15. The method of claim 14 wherein the sample is excited with light from a common coherent radiation source during detection of both elastically and inelastically scattered light from the excited sample.

16. The method of claim 14 wherein the step of exciting excites the sample with different coherent radiation sources during the step of detecting elastically scattered radiation and the step of detecting inelastically scattered radiation from the sample.

17. The method of claim 14 further including the step of performing a correlation between results of the step of detecting elastically scattered radiation from the excited sample and results of the step of detecting inelastically scattered radiation from the excited sample while the condition is changed.

18. The method of claim 14 further including the step of associating a change in a chemical property of a species in the sample with a changes in the condition based on results of the steps of detecting elastically scattered radiation from the excited sample and detecting inelastically scattered radiation from the excited sample.

19. The method of claim 14 wherein the steps of exciting and detecting are repeated to evaluate one of manufacturability, stability, shelf life, quality control, quality assurance or formulation of the sample.

20. The method of claim 14 wherein the steps of positioning, exciting, detecting and removing are performed for a protein suspension, a biopharmaceutical or for one or more of an enzyme, a protein, a DNA sequence, an RNA sequence, a vaccine, a virus and a virus-like particle.

21. The method of claim 14 further including the step of deriving a physical property of the sample from the detected elastically scattered radiation and the step of deriving a chemical property of the sample from the detected inelastically scattered radiation.

22. The method of claim 21 wherein the step of deriving a physical property includes deriving a particle size or polydispersity value and the step of deriving a chemical property includes deriving a measure of chemical identification or molecular structure.

23. The method of claim 21 wherein the steps of positioning, exciting, detecting and removing are performed for a protein, and wherein the step of deriving a physical property includes deriving a protein aggregation size distribution and the step of deriving a chemical property includes deriving a protein secondary and tertiary structural information from a Raman measurement.

24. The method of claim 23 wherein the step of deriving a chemical property includes deriving information about protein folding or protein denaturation/renaturation.

25. The method of claim 14, further comprising determining physicochemical properties of the sample from the dynamic light scattering measurement.

26. The method of claim 25, wherein the physicochemical properties are selected from: a protein zeta potential, charge or isoelectric point.

* * * * *